US012336966B2

(12) United States Patent
Alsberg et al.

(10) Patent No.: US 12,336,966 B2
(45) Date of Patent: *Jun. 24, 2025

(54) SECURED MEDICATION TRANSFER SYSTEM

(71) Applicant: Eli Lilly and Company, Indianapolis, IN (US)

(72) Inventors: Keith Daniel Alsberg, Evanston, IL (US); Christopher John DeMaria, Stow, MA (US); Kenneth James Micklash, II, Carmel, IN (US); Gary Harlan Paulsen, Chicago, IL (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/363,981

(22) Filed: Aug. 2, 2023

(65) Prior Publication Data

US 2023/0372198 A1    Nov. 23, 2023

Related U.S. Application Data

(62) Division of application No. 16/323,650, filed as application No. PCT/US2017/047563 on Aug. 18, 2017, now Pat. No. 11,730,678.

(Continued)

(51) Int. Cl.
*A61J 1/14*    (2023.01)
*A61J 1/16*    (2023.01)
(Continued)

(52) U.S. Cl.
CPC ............... *A61J 1/2096* (2013.01); *A61J 1/16* (2013.01); *A61M 5/1782* (2013.01); *A61J 1/1443* (2013.01); *A61J 1/20* (2013.01); *A61J 1/201* (2015.05); *A61J 1/2048* (2015.05); *A61J 1/2058* (2015.05); *A61J 1/2065* (2015.05); *A61J 1/2089* (2013.01); *A61M 2039/1077* (2013.01)

(58) Field of Classification Search
CPC .. A61J 1/2096; A61J 1/16; A61J 1/201; A61J 1/2089; A61J 1/2048; A61J 1/2065; A61J 1/2058; A61J 1/20; A61J 1/1443; A61M 5/1782; A61M 2039/1077
See application file for complete search history.

(56) References Cited

U.S. PATENT DOCUMENTS

| 4,150,673 | A | 4/1979 | Watt |
| 4,619,640 | A | 10/1986 | Potolsky et al. |

(Continued)

FOREIGN PATENT DOCUMENTS

| CN | 2882607 | 3/2007 |
| CN | 101028226 | 9/2007 |

(Continued)

*Primary Examiner* — Kai H Weng
(74) *Attorney, Agent, or Firm* — Jonathan C. Anderson

(57) ABSTRACT

A vial adaptor and needle assembly are disclosed for use with a vial containing a medication, such as insulin. The vial adaptor may include a needle opening configured to receive a needle of a geometrically corresponding needle assembly to withdraw the medication from the vial in a secured manner. The vial adaptor may also include a cleaning passageway configured to receive a cleaning device to clean the vial.

18 Claims, 23 Drawing Sheets

Related U.S. Application Data

(60) Provisional application No. 62/377,853, filed on Aug. 22, 2016.

(51) Int. Cl.
*A61J 1/20* (2006.01)
*A61M 5/178* (2006.01)
*A61M 39/10* (2006.01)

(56) References Cited

U.S. PATENT DOCUMENTS

| | | | |
|---|---|---|---|
| 5,017,186 A * | 5/1991 | Arnold | A61J 1/2096 604/48 |
| 5,429,256 A | 7/1995 | Kestenbaum | |
| 5,620,427 A | 4/1997 | Weschmidt et al. | |
| 5,700,244 A | 12/1997 | Kriesel | |
| 5,725,511 A | 3/1998 | Urrutia | |
| 5,776,103 A | 7/1998 | Kriesel et al. | |
| 5,807,355 A | 9/1998 | Kriesel et al. | |
| 5,957,891 A | 9/1999 | Kriesel et al. | |
| 6,086,560 A | 7/2000 | Kriesel | |
| 6,132,416 A | 10/2000 | Broselow | |
| 6,253,804 B1 | 7/2001 | Safabash | |
| 6,277,095 B1 | 8/2001 | Kriesel et al. | |
| 6,293,159 B1 | 9/2001 | Kriesel et al. | |
| 6,355,019 B1 | 3/2002 | Kriesel et al. | |
| D460,181 S | 7/2002 | Swenson | |
| D460,551 S | 7/2002 | Swenson | |
| D462,761 S | 9/2002 | Swenson | |
| 6,453,956 B2 | 9/2002 | Safabash | |
| 6,500,153 B1 | 12/2002 | Sheppard et al. | |
| 6,591,876 B2 | 7/2003 | Safabash | |
| 6,599,264 B1 | 7/2003 | Erni et al. | |
| 6,749,587 B2 | 6/2004 | Flaherty | |
| 6,874,522 B2 | 4/2005 | Anderson et al. | |
| 6,890,310 B2 | 5/2005 | Fracavilla et al. | |
| 6,890,328 B2 | 5/2005 | Fowles et al. | |
| 7,137,654 B2 | 11/2006 | Segal et al. | |
| 7,354,427 B2 | 4/2008 | Fangrow | |
| 7,615,041 B2 | 11/2009 | Sullivan | |
| 7,806,868 B2 | 10/2010 | DePolo et al. | |
| 7,918,825 B2 | 4/2011 | O'Connor et al. | |
| 7,981,076 B2 | 7/2011 | Sullivan et al. | |
| 8,034,026 B2 | 10/2011 | Grant et al. | |
| 8,122,923 B2 | 2/2012 | Kraus et al. | |
| 8,177,767 B2 | 5/2012 | Kristensen et al. | |
| 8,196,614 B2 | 6/2012 | Kriheli | |
| 8,323,250 B2 | 12/2012 | Chong et al. | |
| 8,356,645 B2 | 1/2013 | Chong et al. | |
| 8,414,522 B2 | 4/2013 | Kamen et al. | |
| 8,449,504 B2 | 5/2013 | Carter et al. | |
| 8,465,461 B2 | 6/2013 | Wu et al. | |
| 8,511,352 B2 | 8/2013 | Kraus et al. | |
| 8,512,309 B2 | 8/2013 | Shemesh et al. | |
| D690,418 S | 9/2013 | Rosenquist | |
| 8,608,723 B2 | 12/2013 | Lev et al. | |
| 8,632,506 B2 | 1/2014 | Steenfeldt-Jensen et al. | |
| 8,728,024 B2 | 5/2014 | Kamen et al. | |
| 8,827,956 B2 | 9/2014 | Banik et al. | |
| 8,870,238 B2 | 10/2014 | Robert et al. | |
| 8,870,832 B2 | 10/2014 | Raday et al. | |
| 8,881,774 B2 | 11/2014 | Lanier, Jr. et al. | |
| D720,451 S | 12/2014 | Denenburg | |
| 8,968,257 B2 | 3/2015 | Dasbach et al. | |
| 9,107,809 B2 | 8/2015 | Garfield et al. | |
| 9,152,829 B2 | 10/2015 | Day et al. | |
| 9,162,027 B2 | 10/2015 | Kamen et al. | |
| 9,173,997 B2 | 11/2015 | Gross et al. | |
| 9,180,242 B2 | 11/2015 | Metzmaker et al. | |
| 9,220,833 B2 | 12/2015 | Robert et al. | |
| D747,472 S | 1/2016 | Bradley | |
| 9,242,042 B2 | 1/2016 | Martin et al. | |
| D801,522 S | 10/2017 | Ben | |
| D832,430 S | 10/2018 | Denenburg | |
| 10,537,495 B2 | 1/2020 | Ivosevic et al. | |
| 2003/0105428 A1 | 6/2003 | Hogan et al. | |
| 2006/0047251 A1 | 3/2006 | Bickford Smith et al. | |
| 2006/0047252 A1 | 3/2006 | Ono | |
| 2006/0235364 A1 | 10/2006 | O'Hare et al. | |
| 2007/0233008 A1 | 10/2007 | Kristensen et al. | |
| 2008/0306439 A1 | 12/2008 | Nelsen | |
| 2008/0311007 A1 | 12/2008 | Helmerson | |
| 2009/0099552 A1 | 4/2009 | Levy et al. | |
| 2009/0177177 A1 | 7/2009 | Zinger et al. | |
| 2010/0036319 A1 | 2/2010 | Drake | |
| 2010/0198183 A1 | 8/2010 | Lanigan et al. | |
| 2010/0217226 A1 | 8/2010 | Shemesh | |
| 2010/0286661 A1 | 11/2010 | Raday | |
| 2011/0087164 A1 | 4/2011 | Mosler | |
| 2011/0208123 A1 | 8/2011 | Greay et al. | |
| 2011/0264037 A1 | 10/2011 | Foshee | |
| 2012/0000569 A1 | 1/2012 | Wiegel | |
| 2012/0029431 A1 | 2/2012 | Hwang et al. | |
| 2012/0053555 A1 | 3/2012 | Ariagno | |
| 2012/0059346 A1 | 3/2012 | Sheppard | |
| 2012/0067429 A1 | 3/2012 | Mosler | |
| 2012/0150129 A1 | 6/2012 | Jin et al. | |
| 2012/0195182 A1 | 8/2012 | Pommereau et al. | |
| 2012/0310203 A1 | 12/2012 | Khaled et al. | |
| 2012/0323210 A1 | 12/2012 | Lev | |
| 2013/0053791 A1 | 2/2013 | Clark | |
| 2013/0053814 A1 | 2/2013 | Mueller-Beckhaus | |
| 2013/0116631 A1 | 5/2013 | Ziman et al. | |
| 2013/0199669 A1 | 8/2013 | Moy | |
| 2013/0211328 A1 | 8/2013 | Plumptre et al. | |
| 2013/0231630 A1 | 9/2013 | Kraus | |
| 2013/0253432 A1 | 9/2013 | Avery et al. | |
| 2013/0292004 A1 | 11/2013 | Ducret et al. | |
| 2013/0296807 A1 | 11/2013 | Lintern et al. | |
| 2014/0257249 A1 | 9/2014 | Witt | |
| 2014/0276649 A1 | 9/2014 | Ivosevic et al. | |
| 2014/0299568 A1 | 10/2014 | Browne | |
| 2015/0051571 A1 | 2/2015 | Lanigan et al. | |
| 2015/0105745 A1 | 4/2015 | Banik et al. | |
| 2015/0123398 A1 | 5/2015 | Sanders et al. | |
| 2015/0151857 A1 | 6/2015 | Lanigan et al. | |
| 2015/0157537 A1 | 6/2015 | Lanigan et al. | |
| 2015/0174320 A1 | 6/2015 | Grant et al. | |
| 2015/0190311 A1 | 7/2015 | Sund | |
| 2015/0246176 A1 | 9/2015 | Navarro et al. | |
| 2015/0265500 A1 | 9/2015 | Russo et al. | |
| 2015/0297881 A1 | 10/2015 | Sanders et al. | |
| 2016/0000653 A1 | 1/2016 | Kramer | |
| 2016/0008536 A1 | 1/2016 | Gravesen et al. | |
| 2016/0038671 A1 | 2/2016 | Kamen et al. | |
| 2016/0051446 A1 | 2/2016 | Lev et al. | |
| 2016/0058667 A1 | 3/2016 | Kriheli | |
| 2016/0206511 A1 | 7/2016 | Garfield et al. | |
| 2017/0007501 A1 | 1/2017 | Schuldt-Lieb et al. | |
| 2017/0189270 A1 | 7/2017 | Liu et al. | |
| 2017/0354571 A1 | 12/2017 | David et al. | |
| 2019/0167526 A1 | 6/2019 | Alsberg | |
| 2019/0321262 A1 | 10/2019 | Chudek et al. | |

FOREIGN PATENT DOCUMENTS

| | | |
|---|---|---|
| EP | 0556618 | 8/1993 |
| EP | 0820778 | 1/1998 |
| GB | 325959 | 3/1930 |
| TW | M294327 | 7/2006 |
| WO | 200047268 | 8/2000 |
| WO | 2010054463 | 5/2010 |
| WO | 10078434 | 7/2010 |
| WO | 2011131779 | 10/2011 |
| WO | 2012010564 | 1/2012 |
| WO | 2016004329 | 1/2016 |

* cited by examiner

ND TRANSFER SYSTEM

SECURED MEDICATION TRANSFER SYSTEM

CROSS REFERENCE TO RELATED APPLICATION

This application is a divisional of U.S. patent application Ser. No. 16/323,650, filed Feb. 6, 2019, which is a National Stage of International Application No. PCT/US2017/047563, filed Aug. 18, 2017, which claims priority to U.S. Provisional Patent Application Ser. No. 62/377,853, filed Aug. 22, 2016, the disclosure disclosures of which are hereby expressly incorporated by reference herein in their entirety.

FIELD OF THE DISCLOSURE

The present disclosure relates to a system for transferring a medication in a secured manner, and to a method for using the same.

BACKGROUND OF THE DISCLOSURE

A vial 10 that is configured to hold a medication 11, such as insulin or another medication, is shown in FIG. 1. The illustrative vial 10 incudes a relatively wide flange or rim 12, a relatively narrow neck 14 beneath flange 12, and a slanted shoulder 16 that widens beneath neck 14. The upper end of the illustrative vial 10 also includes a septum or stopper 18 (e.g., a rubber stopper) that seals and protects the medication in vial 10. Stopper 18 may be generally T-shaped in cross-section, such that stopper 18 rests above flange 12 of vial 10 and extends downward into vial 10 toward neck 14. Flange 12 includes a crimp seal 17 (e.g., aluminum material) that extends around flange 12 and stopper 18 to secure stopper 18 to vial 10 while providing top access to stopper 18 for needle 22. A protective lid or cap 19 is coupled to the top of vial 10 over stopper 18 and is removed, such as with a user's fingers, prior to piercing stopper 18 with needle 22.

A traditional syringe 20 is also shown in FIG. 1. The illustrative syringe 20 includes plunger 24 and a needle 22 that protrudes from syringe 20 by a length L along axis A. Syringe 20 includes a hub 23 at a distal end that secures needle 22 to syringe 20. Hub 23 with needle 22 may be removably coupled to the body of syringe 20, such as via a standardized connection (e.g., Luer-Lok® connection fitting), or may be integrally formed with syringe 20. In use, needle 22 of syringe 20 punctures stopper 18 along axis A (or at a small angle relative to axis A), and plunger 24 of syringe 20 is pulled to withdraw the medication from vial 10. In certain embodiments, syringe 20 is used to transfer the medication to a delivery device (not shown), such as an insulin pump for example. The transfer syringe 20 may be an independent component that is separate from the delivery device, as shown in FIG. 1, or a component that is part of a delivery device such as a pump reservoir. In other embodiments, syringe 20 is used to deliver the medication directly to a patient.

The concentration of the medication in vial 10 may vary. With respect to insulin, for example, vial 10 may contain 100 units of insulin per milliliter (mL) of liquid (i.e., U-100 insulin), 200 units of insulin per mL of liquid (i.e., U-200 insulin), 500 units of insulin per mL of liquid (i.e., U-500 insulin), or another suitable insulin concentration. The higher-concentration medications may have certain advantages for the patient, such as extended usage times and smaller delivery devices, for example. However, if a higher-concentration medication is mistaken for a lower-concentration medication, the patient may be susceptible to overdose or hypoglycemia.

SUMMARY

The present disclosure provides a vial adaptor and needle assembly configured for use with a vial containing a medication, such as insulin. The vial adaptor may include a needle opening configured to receive a needle of a geometrically corresponding needle assembly hub to withdraw the medication from the vial in a secured manner. The vial adaptor may also include a cleaning passageway configured to receive a cleaning device to clean the vial stopper while blocking access to the stopper with a needle through the cleaning passageway. In some embodiments, the vial adapter is configured to reduce the likelihood that a user transfers an incorrect insulin concentration into a delivery device.

According to an embodiment of the present disclosure, a vial adaptor is provided for use with a vial containing a medication and a needle assembly having a needle. The vial adaptor includes: a substantially hollow body configured to couple with the vial; a needle opening in the body, the needle opening being arranged along an axis and being sized and shaped to receive the needle along the axis to withdraw the medication from the vial; a cleaning passageway in the body, the cleaning passageway being sized and shaped to receive a cleaning device to clean the vial; and a shroud extending outward from the body to block needle insertion into the vial through the cleaning passageway.

In certain embodiments, a lower end of the body includes a generally cylindrical side wall and an upper end of the body includes an upper wall, the shroud extending radially outward beyond the cylindrical side wall of the lower end of the body.

In certain embodiments, the shroud extends continuously from the upper wall of the body.

In certain embodiments, the shroud extends from the axis of the needle opening by a distance of about 20 millimeters to about 30 millimeters.

In certain embodiments, the cleaning passageway is offset from the axis of the needle opening between a first angle greater than 50 degrees and a second angle less than 150 degrees. The first angle may be about 60 degrees to about 70 degrees, and the second angle may be about 110 degrees to about 120 degrees.

In certain embodiments, an inlet to the cleaning passageway is located in a side wall of the body, the side wall extending radially outward from a lower end of the body to an upper end of the body such that the inlet to the cleaning passageway also extends radially outward from a lower end of the inlet to an upper end of the inlet.

In certain embodiments, an inlet to the cleaning passageway includes a notch. The notch may be positioned closer to a lower end of the inlet than an upper end of the inlet.

In certain embodiments, an inlet to the cleaning passageway is larger than an inlet to the needle opening.

In certain embodiments, the needle opening follows a linear pathway and the cleaning passageway follows a non-linear pathway.

In certain embodiments, the needle opening is formed in a rim, the rim having a tapered outer surface and at least one protrusion for coupling the rim to the body.

In certain embodiments, a needle assembly is provided including a hub having a keyed outer profile that matches the shape of the needle opening.

According to another embodiment of the present disclosure, a vial adaptor is provided for use with a vial containing a medication and having a relatively wide flange, a relatively narrow neck beneath the flange, and a slanted shoulder beneath the neck. The vial adaptor includes: a substantially hollow body; a needle opening in the body, the needle opening being sized and shaped to receive a needle to withdraw the medication from the vial; and a coupling assembly configured to couple the body to the vial, the coupling assembly including: a plurality of first fingers, each first finger configured to flex over the rim of the vial and release towards the neck beneath the rim of the vial; and a plurality of second fingers configured to contact the shoulder of the vial to bias the plurality of first fingers toward the rim of the vial.

In certain embodiments, each second finger is shorter than each first finger.

In certain embodiments, the body is sized to cover substantially the entire vial. The body may be at least partially transparent such that the vial is visible through the body.

In certain embodiments, the vial adaptor further includes a passageway in the body, the passageway being sized and shaped to at least one of receive a cleaning device to clean the vial and provide access to a cap of the vial for removal of the cap, and a shroud extending outward from the body to block needle insertion into the vial through the passageway.

According to yet another embodiment of the present disclosure, a method is provided for using a vial adaptor coupled to a vial. The method includes the steps of: cleaning a stopper of the vial by inserting a disinfectant-containing cleaning device through a cleaning passageway of the vial adaptor; and withdrawing a medication from the vial by inserting a needle through a needle opening of the vial adaptor and into the stopper of the vial.

In certain embodiments, the cleaning passageway is offset from the needle opening between a first angle greater than 50 degrees and a second angle less than 150 degrees. In certain embodiments, the method further comprises, prior to the cleaning, removing a cap from the vial through the cleaning passageway.

In certain embodiments, the method further includes the step of blocking needle insertion into the vial through the cleaning passageway by contacting a shroud around the cleaning passageway.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
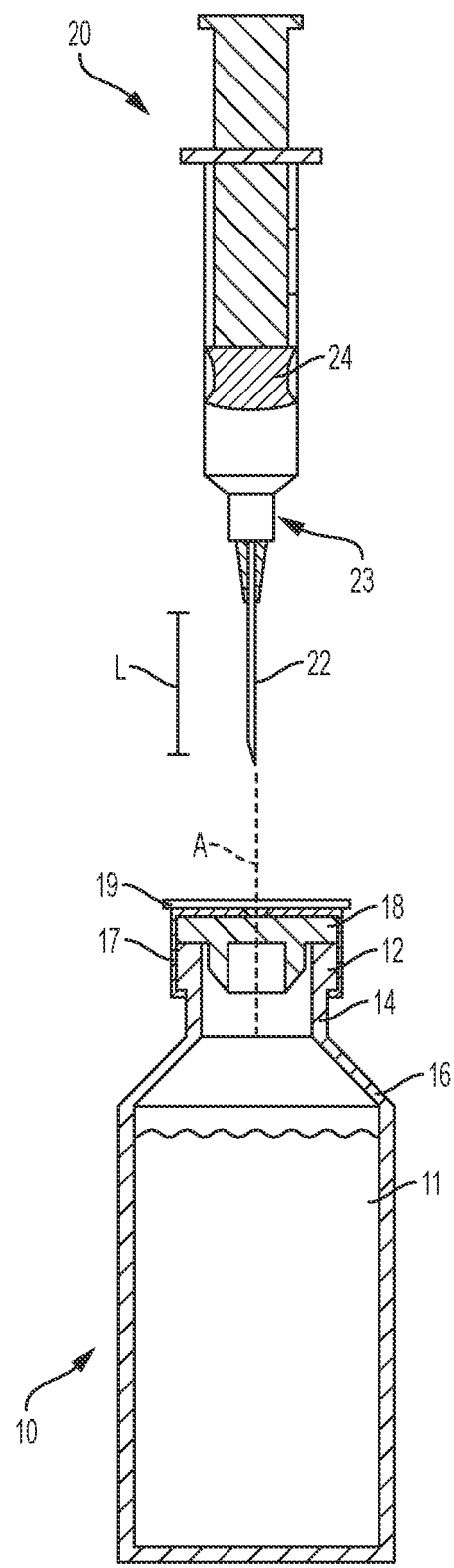
FIG. 1 is a cross-sectional view of a vial containing a medication and a transfer syringe.
Figure 2:
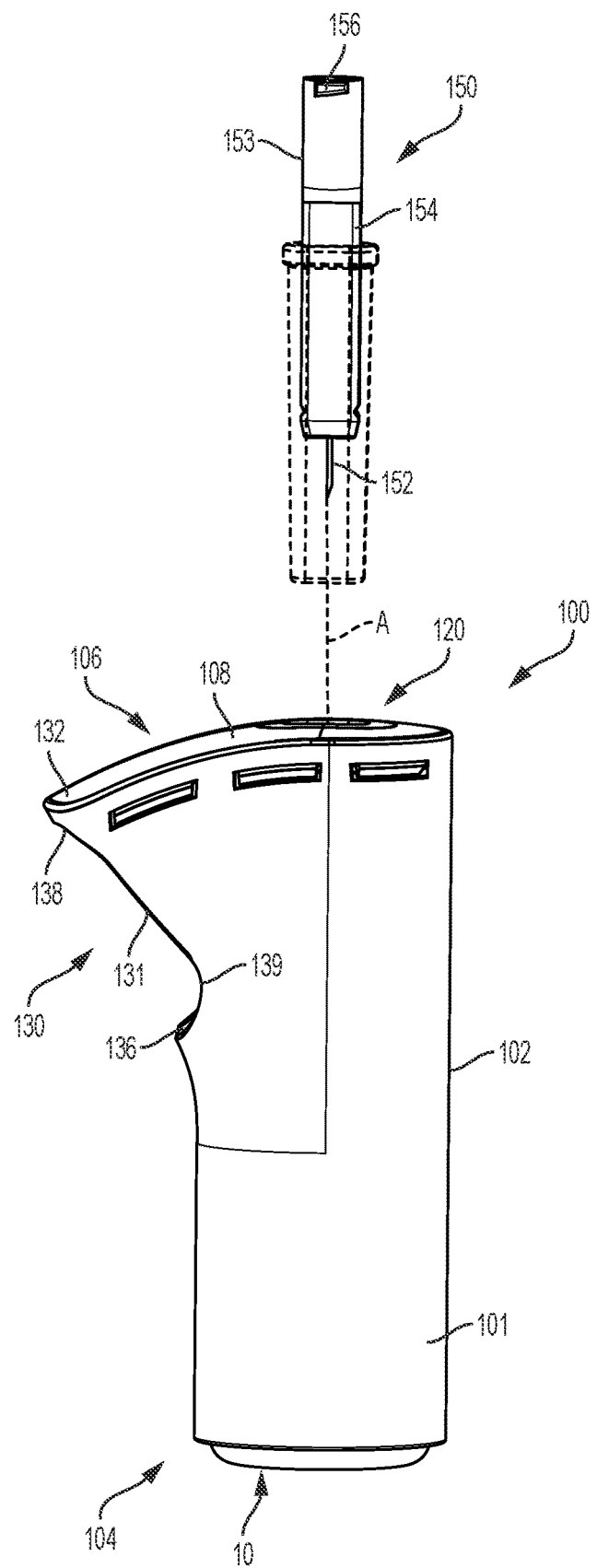
FIG. 2 is a front elevational view of a first exemplary vial adaptor coupled to a vial and a geometrically corresponding needle assembly, the vial adaptor shown in a non-use position.

Referring initially to FIGS. 2-10, a first exemplary vial adaptor 100 is shown for use with vial 10, and a geometrically corresponding needle assembly 150 is shown for use with syringe 20 (FIG. 1) or another transfer assembly (e.g., an integrated insulin pump).

The illustrative vial adaptor 100 includes a substantially hollow body 101 with a generally cylindrical and vertical side wall 102 and a generally flat and horizontal upper wall 108. In the illustrated embodiment of FIG. 9, side wall 102 and upper wall 108 are separate components that are coupled together to form body 101, such as by providing windows 140 in side wall 102 that receive corresponding locking tabs 142 from upper wall 108. It is also within the scope of the present disclosure for side wall 102 and upper wall 108 to be integrally formed together. Side wall 102 and/or upper wall 108 of body 101 may be transparent to allow visibility inside vial adaptor 100. Side wall 102 and/or upper wall 108 of body 101 may also be color-coded or otherwise labeled to visually associate vial adaptor 100 with the corresponding vial 10.

Figure 3:
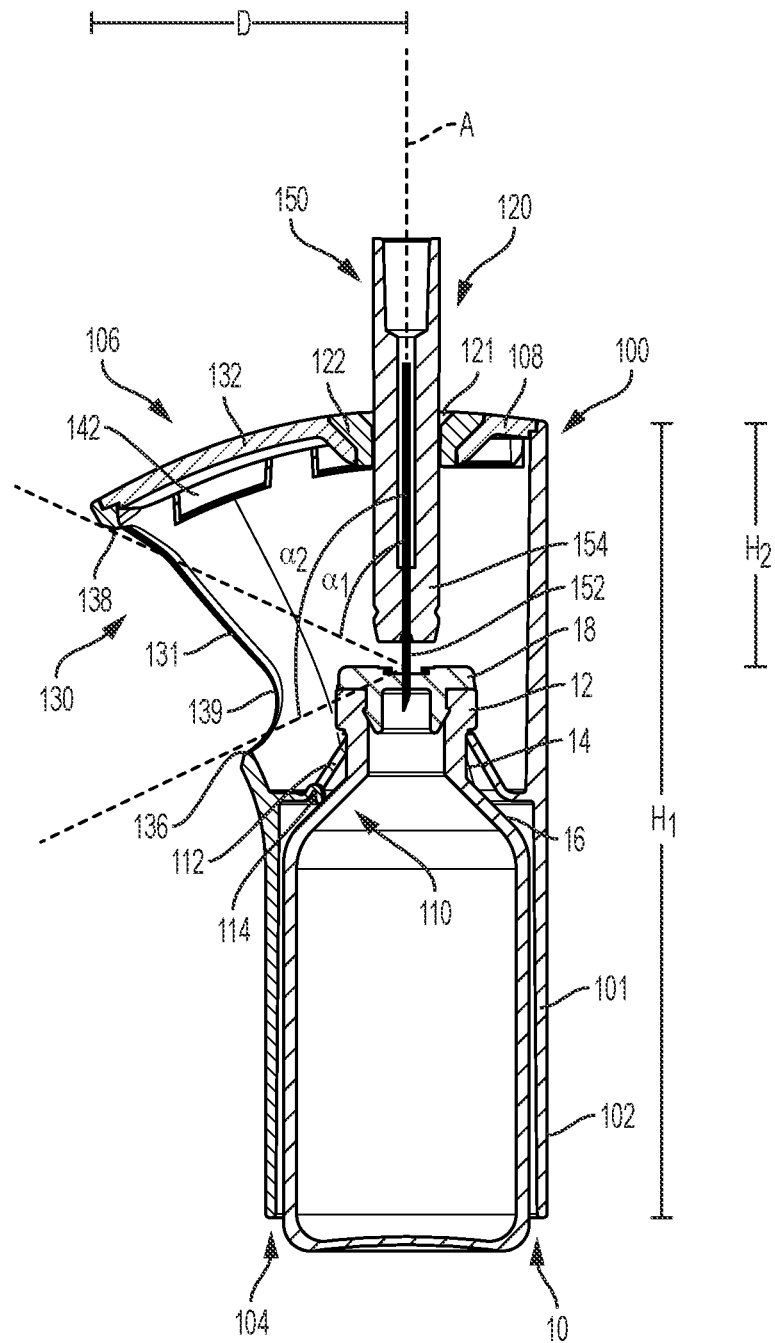
FIG. 3 is a cross-sectional view of the vial adaptor and the needle assembly of FIG. 2 shown in a use position.
Figure 4:
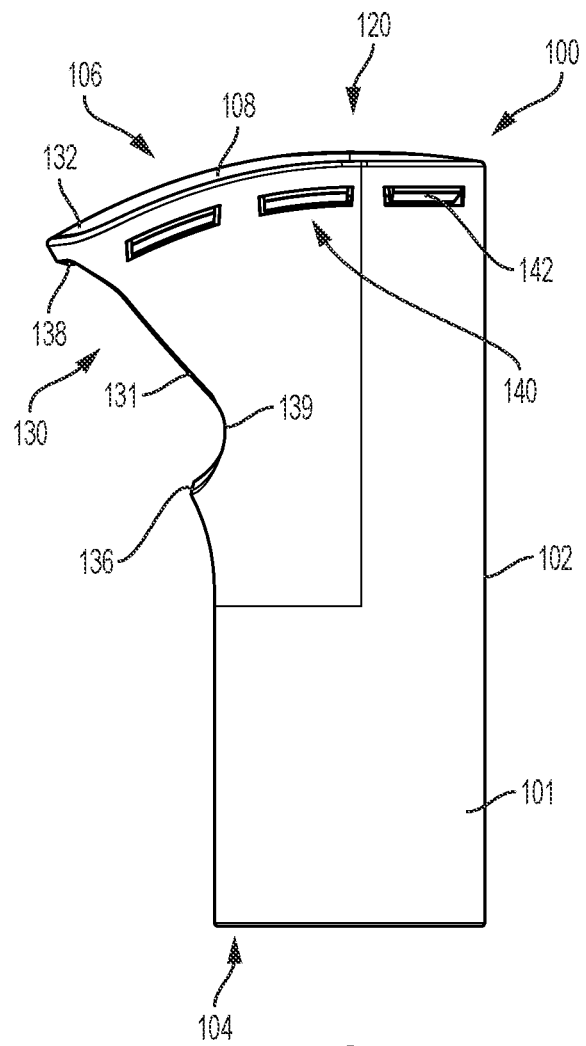
FIG. 4 is a front elevational view of the vial adaptor of FIG. 2.
Figure 5:
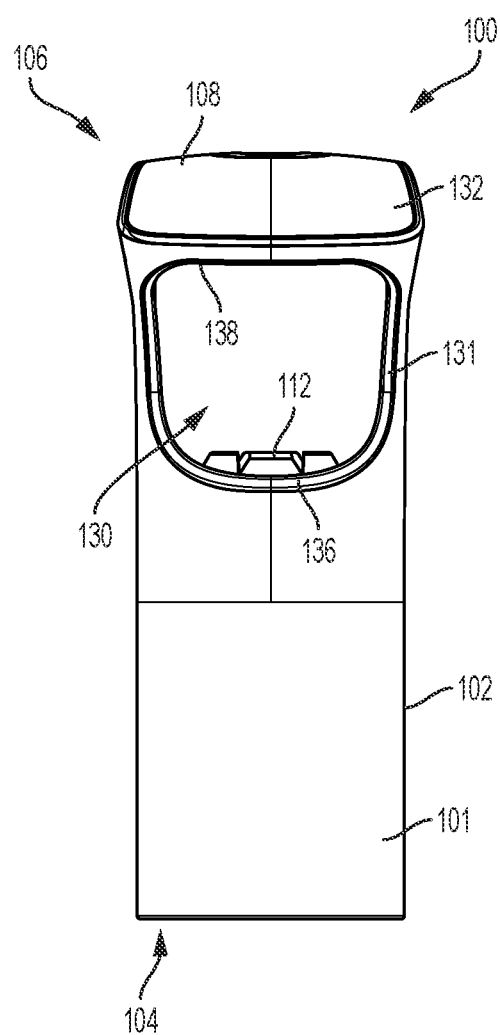
FIG. 5 is a left side elevational view of the vial adaptor of FIG. 2.
Figure 6:
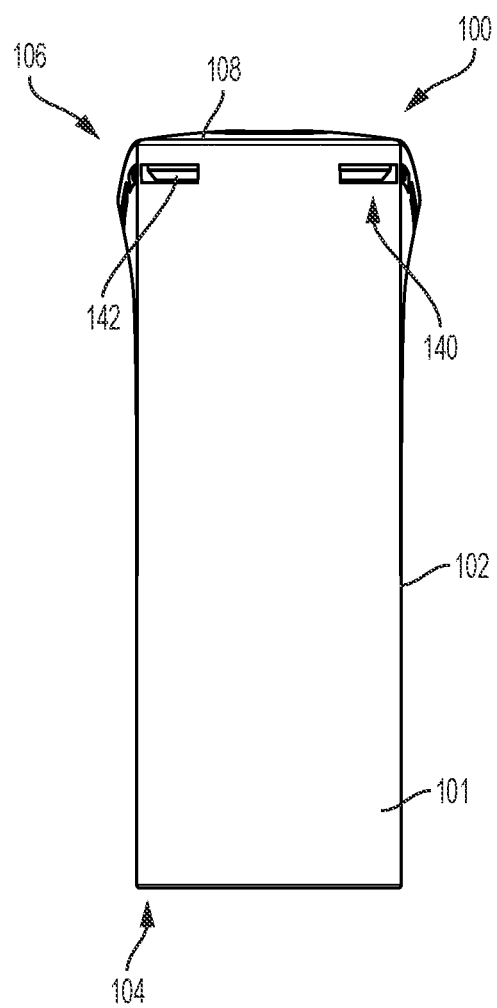
FIG. 6 is a right side elevational view of the vial adaptor of FIG. 2.
Figure 7:
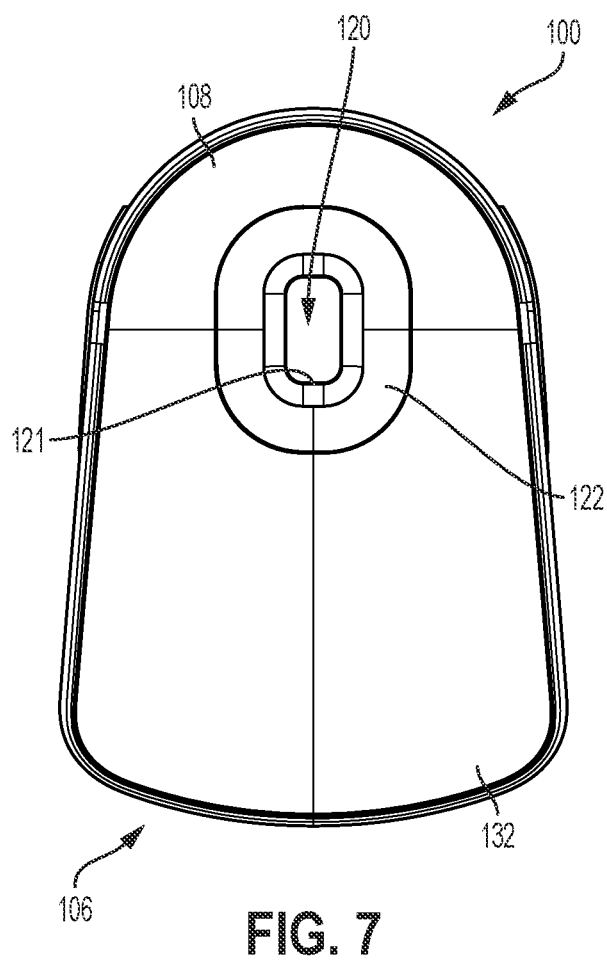
FIG. 7 is a top plan view of the vial adaptor of FIG. 2.
Figure 8:
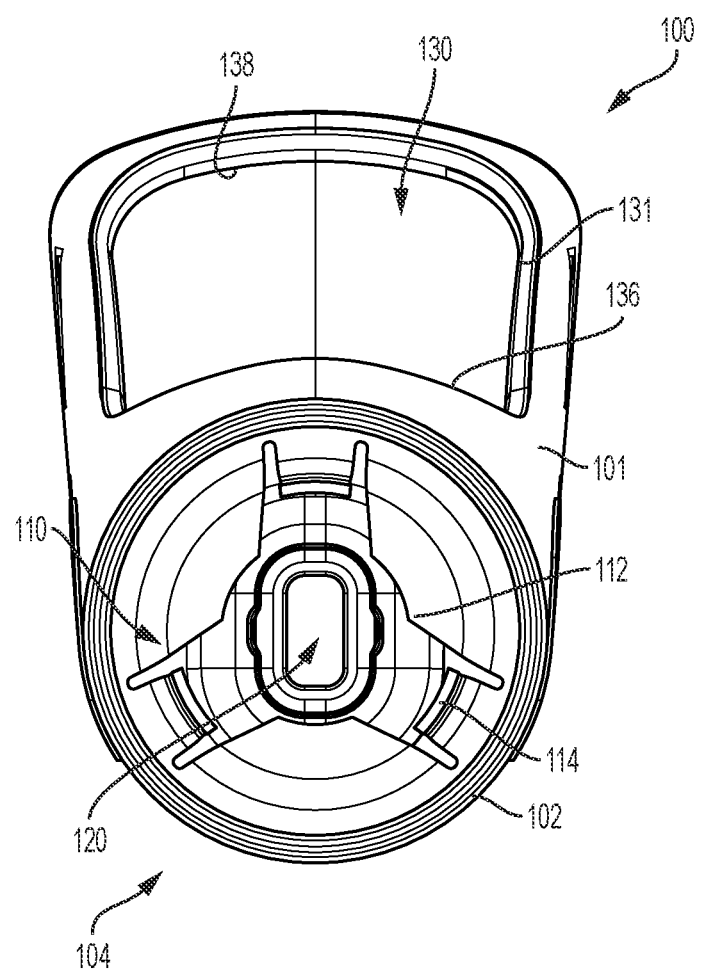
FIG. 8 is a bottom plan view of the vial adaptor of FIG. 2.
Figure 9:
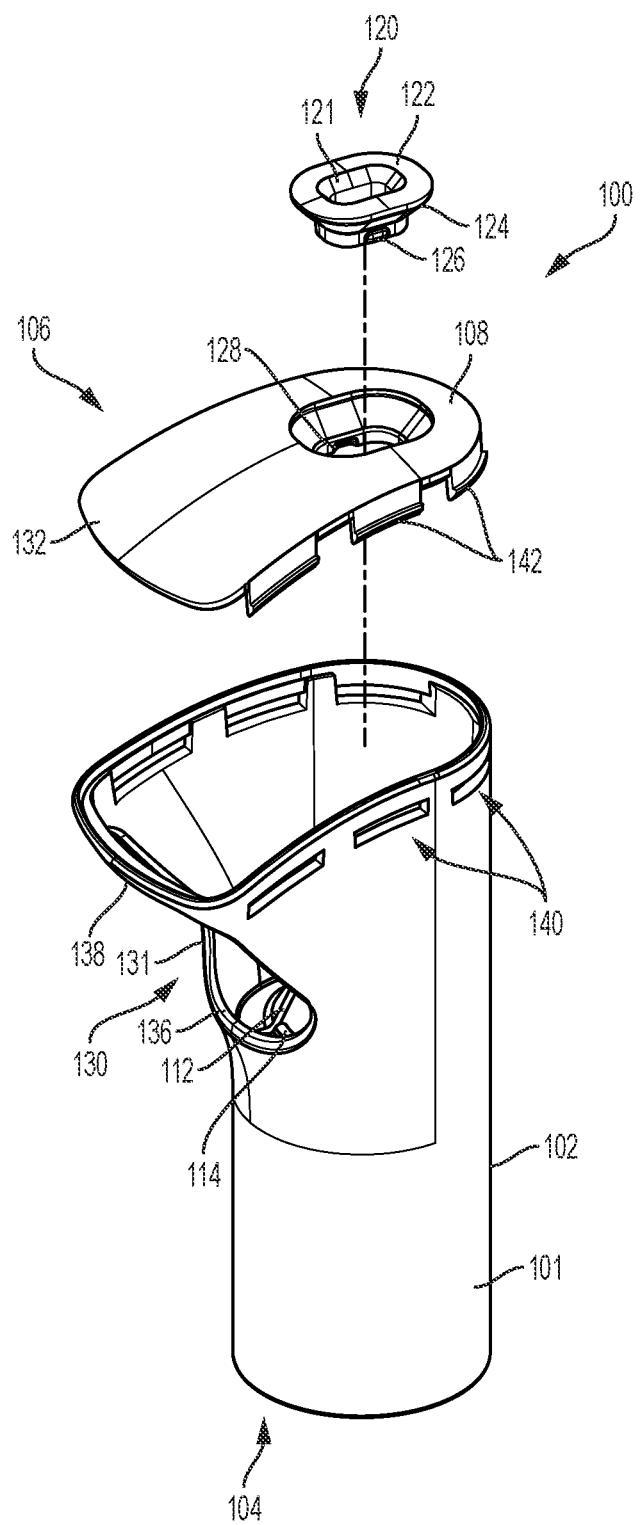
FIG. 9 is an exploded perspective view of the vial adaptor of FIG. 2.
Figure 10:
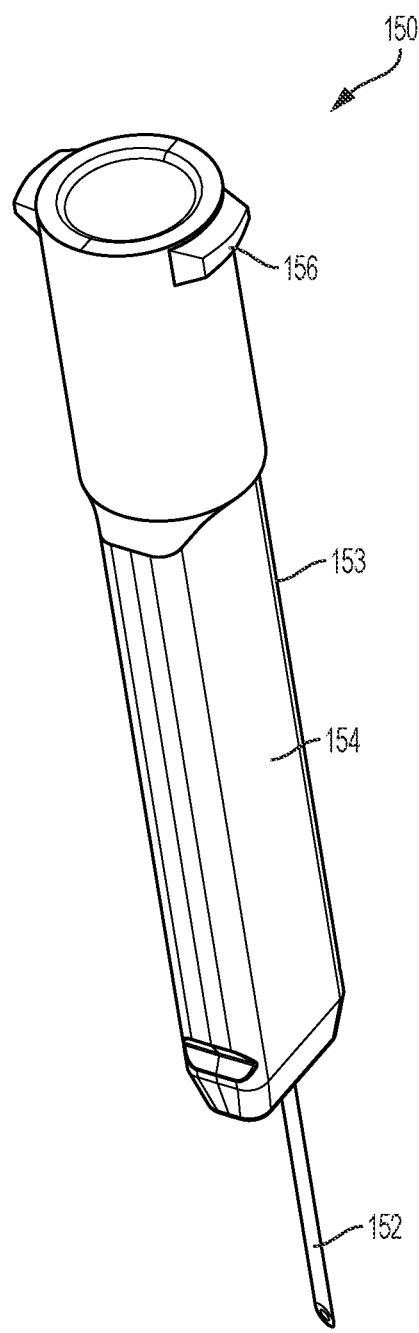
FIG. 10 is a perspective view of the needle assembly of FIG. 2.

Vial adaptor 100 has a lower end 104 that extends onto vial 10 and an upper end 106 that extends above vial 10. Vial adaptor 100 also has a total height $H_1$ measured between lower end 104 and upper end 106 along axis A, as shown in FIG. 3. Side wall 102 of the illustrative vial adaptor 100 covers substantially the entire vial 10, so the total height $H_1$ of vial adaptor 100 exceeds the height of vial 10 alone. For example, the total height $H_1$ of vial adaptor 100 may vary from about 70 millimeters (mm) to about 80 mm, such as about 73 mm for example. Of course, this total height $H_1$ may vary to accommodate vials 10 of different sizes. It is also within the scope of the present disclosure that side wall 102 may only partially cover vial 10.

The illustrative vial adaptor 100 includes a ring-shaped coupling assembly 110 configured to couple vial adaptor 100 to vial 10. The coupling between vial adaptor 100 and vial 10 may be performed by the supplier of vial 10 and may be permanent in nature to reduce the likelihood of subsequent removal by the end user or another intermediate party. Coupling assembly 110 may be integrally formed with side wall 102 of vial adaptor 100, or coupling assembly 110 may be a separate component that is fixedly coupled (e.g., welded, adhered, fastened) to side wall 102 of vial adaptor 100. The illustrative coupling assembly 110 includes a first set of relatively long and flexible fingers 112 and a second set of relatively short, U-shaped, and flexible fingers 114, both of which extend radially inward from side wall 102 of vial adaptor 100 toward vial 10. As vial adaptor 100 is pressed downward onto vial 10, each finger 112 is designed to flex radially outwardly around flange 12 (including the cap and surrounding crimp seal of FIG. 1) of vial 10 and then snap back or release toward neck 14, which locks vial adaptor 100 in place beneath flange 12 and the crimp seal of vial 10. At the same time, each finger 114 is designed to compress against shoulder 16 of vial 10. Each compressed finger 114 is thus positioned against the narrowing, slanted shoulder 16 toward neck 14 to apply a continuous upward force to vial adaptor 100 and maintain fingers 112 against the underside of flange 12. The flexibility of fingers 112, 114, may allow coupling assembly 110 to accommodate vials 10 of different shapes and sizes. Alternatively, fingers 114 are rigid fingers 114 that abut shoulder 16 to apply a hard stop against shoulder 16, thereby applying the continuous upward force to vial adaptor 100 and maintaining fingers 112 against the underside of flange 12.

The illustrative vial adaptor 100 also includes a needle port or opening 120 that extends through upper wall 108 and follows a linear pathway along axis A. Inlet 121 of needle opening 120 may be defined by a separate rim 122 that is coupled (e.g., welded, adhered, fastened) to upper wall 108, or inlet 121 of needle opening 120 may be formed directly by upper wall 108. In the illustrated embodiment of FIG. 9, rim 122 includes a tapered outer surface 124 that matches the tapered contour of upper wall 108 and one or more protrusions 126 configured to snap into corresponding recesses 128 in upper wall 108. An optional cap or lid (not shown) may also be provided to selectively cover inlet 121 of needle opening 120.

Needle opening 120 is sized and shaped to accommodate a geometrically corresponding hub 153 of needle assembly 150, as discussed further below, but not a needle hub of a traditional or commonly used syringe (e.g., standard hub 23 of syringe 20 of FIG. 1). For example, needle opening 120 may be sized and shaped to accommodate needle assembly 150 associated with U-200 insulin, but not a standard syringe 20 typically used with U-100 insulin vials. As a result, needle opening 120 may reduce the likelihood that the standard syringe 20 associated with U-100 insulin is used to withdraw an improper or unintended medication from vial 10, in this example U-200 insulin. Because the hub 23 of standard syringe 20 is typically circular in shape, needle opening 120 may be sized smaller than hub 23 of syringe 20 and/or may be keyed or non-circular in shape to prevent insertion of hub 23 of syringe 20. In the illustrated embodiment of FIG. 7, needle opening 120 is rectangular-shaped with rounded corners, but it is also within the scope of the present disclosure for needle opening 120 to be oval-shaped, triangular-shaped, cross-shaped, star-shaped, or another suitable shape that is not compatible with a standard needle hub 23. Also, in assembly, needle opening 120 of vial adaptor 100 is spaced apart from stopper 18 of vial 10 by a sufficient height $H_2$ (which is less than the total height $H_1$ of vial adaptor 100) to prevent needle 22 of the standard syringe 20 (FIG. 1) from reaching stopper 18 of vial 10 when hub 23 abuts upper wall 108 or rim 122 of vial adaptor 100. Stated differently, the height $H_2$ between needle opening 120 and stopper 18 may exceed the length L of needle 22 of the standard syringe 20 (FIG. 1). For example, the height $H_2$ may vary from about 15 mm to about 25 mm, such as about 20 mm. The size and shape of needle opening 120 and the height $H_2$ of vial adaptor 100 may be adjusted depending on the size and shape of the particular syringe 20 or other standard transfer assembly for which access prevention is desired.

The illustrative vial adaptor 100 further includes a cleaning passageway 130 that is at least partially surrounded by shroud 132. Inlet 131 of cleaning passageway 130 is shown extending through side wall 102 of body 101, but this location may vary. Shroud 132 is shown extending radially outward from axis A as a continuous extension of upper wall 108 of body 101, but this location may also vary. In the illustrated embodiment of FIG. 3, side wall 102 deviates radially outward from lower end 104 to upper end 106 to follow the path of shroud 132. As a result, inlet 131 of cleaning passageway 130 that is defined by side wall 102 also extends radially outward from lower end 136 of inlet 131 to upper end 138 of inlet 131. Inlet 131 of cleaning passageway 130 may also include a notch 139 to facilitate user access. In the illustrated embodiment of FIG. 3, the notch 139 is positioned closer to lower end 136 of inlet 131 than upper end 138 of inlet 131. In the illustrated embodiment, lower end 136 is curved radially outwardly to facilitate access to the vial cap 19 (FIG. 1) such that a user may remove cap with the user's finger or a tool. For example, the widened space between lower end 136 and stopper 18 shown in FIG. 3 allows a user to insert a finger or tool to apply an upward force to the overhanging portion of cap 19 to pop cap 19 off of vial 10 prior to use. In other embodiments, lower end 136 is flush with the side wall 102.

Cleaning passageway 130 is distinct from needle opening 120 of vial adaptor 100. Cleaning passageway 130 is sized and shaped to allow a cleaning device (e.g., pad, wipe, swab) containing a disinfectant (e.g., alcohol), along with a user's finger, if necessary, to access and clean stopper 18 of vial 10 before use. Cleaning passageway 130 may also be used to remove any seal or cover from stopper 18 of vial 10 before use, as described above. Inlet 131 of cleaning passageway 130 is illustratively larger than inlet 121 of needle opening 120 to accommodate such cleaning devices and the user's finger, if necessary.

In the illustrated embodiment, unlike needle opening 120, cleaning passageway 130 is not intended to allow a needle to access stopper 18, such as the needle of syringe 20 (FIG. 1), needle assembly 150 (FIG. 2), or another medication transfer assembly. Therefore, cleaning passageway 130 and/or shroud 132 are sized and shaped to block unwanted insertion of a needle through stopper 18 via passageway 130. Accordingly, needle opening 120 provides needle access to stopper 18 while shroud 132 blocks needle access to stopper 18 through passageway 130. Shroud 132 may protrude from axis A by a distance D (FIG. 3) of about 20 mm to about 30 mm, such as about 27 mm for example. As a result, access to stopper 18 of vial 10 through the cleaning passageway 130 may be offset from axis A between a first angle $\alpha_1$ measured through upper end 138 of inlet 131 and a second angle $\alpha_2$ measured through lower end 136 of inlet 131. The first angle $\alpha_1$ may be greater than about 50 degrees, more specifically about 50 degrees to about 80 degrees, and even more specifically about 60 degrees to about 70 degrees. The second angle $\alpha_2$ may be less than about 150 degrees, more specifically about 90 degrees to about 150 degrees, and even more specifically about 110 degrees to about 120 degrees. The size and shape of cleaning passageway 130 and/or shroud 132 may be adjusted depending on the size and shape of the particular syringe 20, needle, or other transfer assembly for which access prevention is desired. It is also within the scope of the present disclosure for cleaning passageway 130 to follow a non-linear pathway to further block insertion of a needle through stopper 18 via passageway 130.

The illustrative needle assembly 150 has a hub 153 and a needle/cannula 152 coupled to hub 153. Hub 153 has a keyed outer profile 154 that specifically matches the shape of needle opening 120 in the geometrically corresponding vial adaptor 100. Because needle opening 120 in the illustrative vial adaptor 100 is rectangular-shaped, the outer profile 154 of the corresponding needle hub 153 is also rectangular-shaped, but other shapes may be provided, as discussed above. Needle assembly 150 may be removably coupled to syringe 20 of FIG. 1 (with the standard hub 23 removed) or another standard transfer assembly. In one embodiment, syringe 20 has a female Luer-Lok® connection fitting (not shown), and hub 153 of needle assembly 150 has a male Luer-Lok® connection fitting 156. Other suitable connections (e.g., threaded connections) may be used to removably couple needle assembly 150 to syringe 20. It is also within the scope of the present disclosure for needle assembly 150 to be integrally formed with or permanently coupled to a syringe. The syringe used with needle assembly 150 may be calibrated or scaled based on the specific medication concentration in vial 10, in this example U-200 insulin.

In use, needle assembly 150 is coupled to a syringe (e.g., syringe 20 of FIG. 1 with hub 23 removed) or another transfer device. If necessary, cap 19 (FIG. 1) of vial 10 is removed through cleaning passageway 130, and stopper 18 is cleaned with a disinfectant. Next, needle assembly 150 is inserted into needle opening 120 of the corresponding vial adaptor 100 in a keyed manner, as shown in FIG. 3. In this position, needle 152 of needle assembly 150 is able to reach and puncture stopper 18 of vial 10 along axis A to withdraw the intended medication from vial 10, in this example U-200 insulin. Finally, the withdrawn medication is transferred to a delivery device (not shown), such as an insulin pump, or delivered directly to the patient. The delivery device may include a keyed interface that matches the outer profile of needle hub 153 to receive the insulin into a reservoir of the device.

A set of different vial adaptors 100 and corresponding needle assemblies 150 may be provided for each available medication concentration in vial 10 (FIG. 1), or at least for higher-concentration medications. For each concentration, the shape of needle opening 120 in vial adaptor 100 and outer profile 154 of the corresponding needle assembly 150 may vary. If the rectangular-shaped opening 120 and needle assembly 150 shown in FIGS. 2-10 are provided for use with vial 10 containing U-200 insulin, for example, a differently-shaped needle opening 120 and needle assembly 150 may be provided for use vial 10 containing U-500 insulin. For ease of manufacturing, the different vial adaptors 100 may be substantially identical in size and shape, except for the provision of different rims 122 that form differently-shaped needle openings 120. The height $H_2$ of vial adaptor 100 may also vary for different insulin concentrations.

Figure 11:
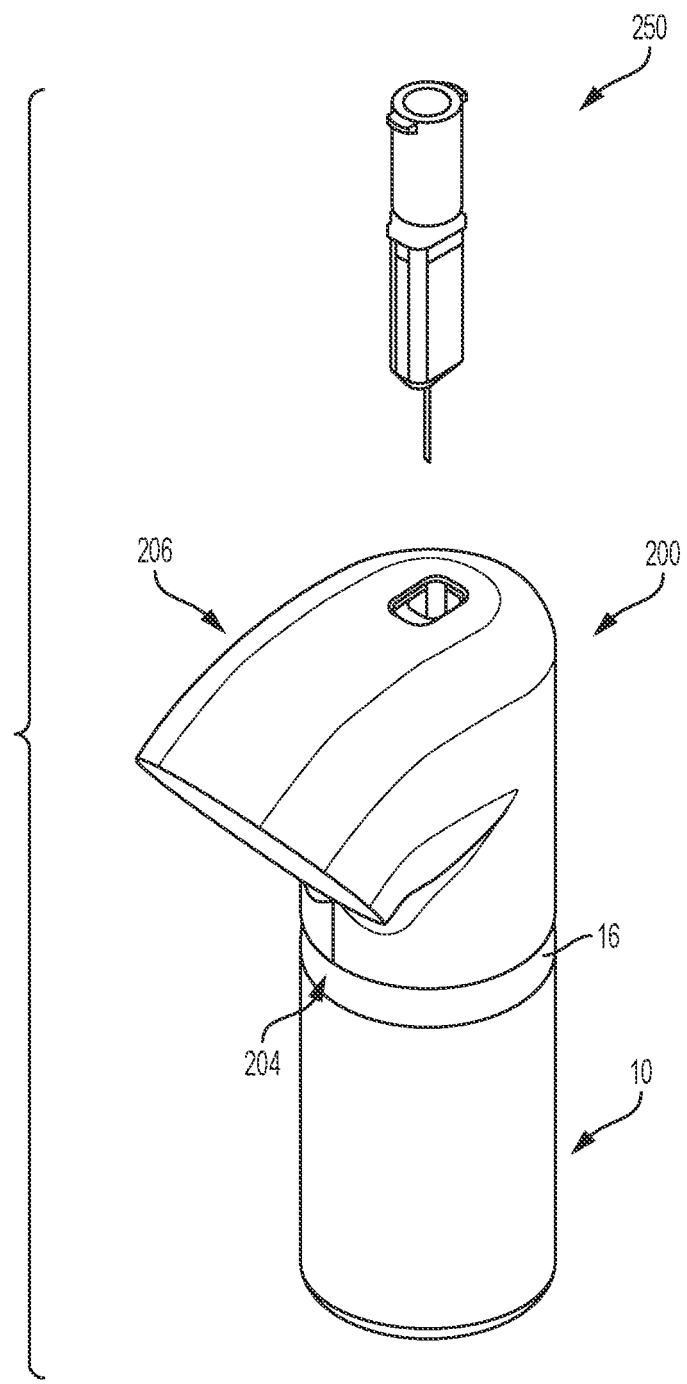
FIG. 11 is a perspective view of a second exemplary vial adaptor coupled to a vial and a geometrically corresponding needle assembly, the vial adaptor shown in a non-use position.
Figure 12:
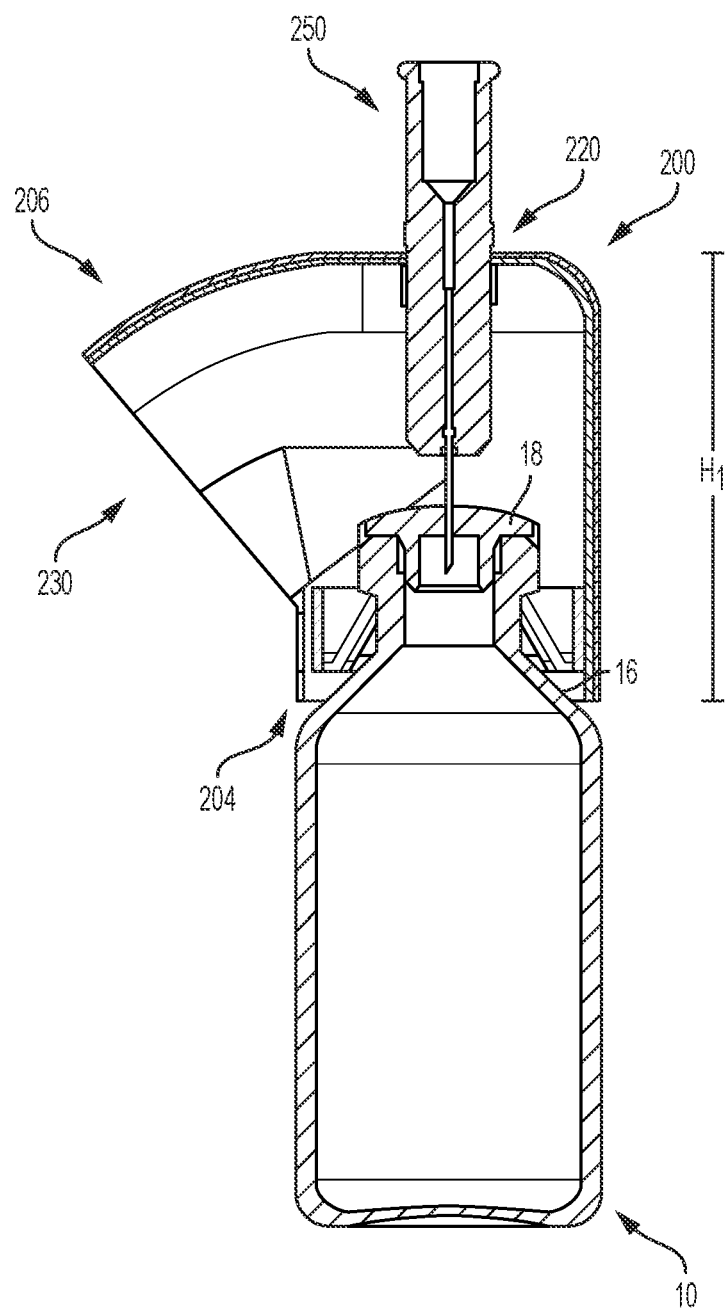
FIG. 12 is a cross-sectional view of the vial adaptor and the needle assembly of FIG. 11 shown in a use position.

Referring next to FIGS. 11 and 12, a second exemplary vial adaptor 200 and needle assembly 250 are shown for use with vial 10. Vial adaptor 200 and needle assembly 250 are similar to the above-described vial adaptor 100 and needle assembly 150, with like reference numerals identifying like elements, except as described below. Rather than covering substantially the entire vial 10, side wall 202 of the illustrative vial adaptor 200 extends only to shoulder 16 of vial 10, as shown in FIG. 12. In this embodiment, the total height $H_1$ of vial adaptor 200 measured between the shortened lower end 204 and upper end 206 may vary from about 30 mm to about 40 mm, such as about 34 mm. The total height $H_1$ of vial adaptor 200 may be less than the height of vial 10. The illustrative vial adaptor 200 includes a needle opening 220 that follows a linear pathway to vial 10 and a cleaning passageway 230 that follows a non-linear pathway to vial 10.

Figure 13:
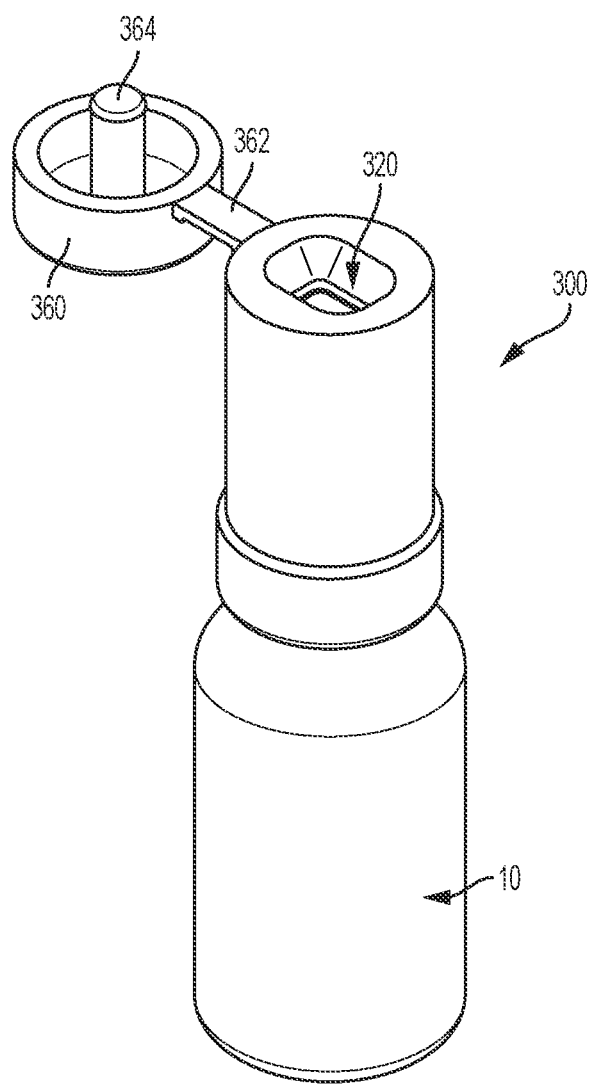
FIG. 13 is a perspective view of a third exemplary vial adaptor coupled to a vial.
Figure 14:
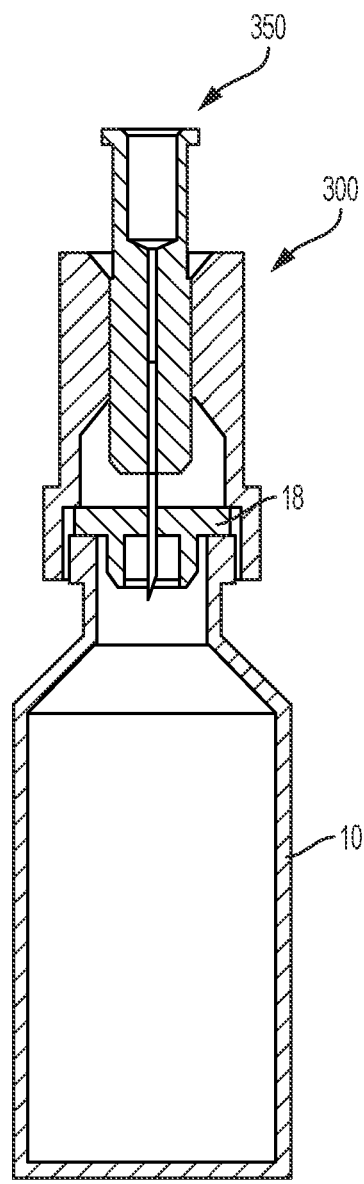
FIG. 14 is a cross-sectional view of the vial adaptor of FIG. 13 and a geometrically corresponding needle assembly shown in a use position.

Referring next to FIGS. 13 and 14, a third exemplary vial adaptor 300 and needle assembly 350 are shown for use with vial 10. Vial adaptor 300 and needle assembly 350 are similar to the above-described vial adaptors 100, 200 and needle assembly 150, 250, with like reference numerals identifying like elements, except as described below. The illustrative vial adaptor 300 includes a lid or cap 360 configured to selectively cover needle opening 320. Cap 360 includes a flexible hinge 362 coupled to body 301 of vial adaptor 300 and a plug 364 sized for receipt in needle opening 320 of vial adaptor 300. When cap 360 is closed, plug 364 may be sized to contact stopper 18 of vial 10 to prevent foreign material from accessing stopper 18. Plug 364 may also include an anti-microbial material on its surface to clean stopper 18 of vial 10 when cap 360 is closed. The illustrative vial adaptor 300 lacks a cleaning passageway distinct from needle opening 320, so needle opening 320 may be used for both cleaning vial 10 and withdrawing medication from vial 10. Thus, when cap 360 is opened, as shown in FIG. 13, stopper 18 of vial 10 may be exposed through needle opening 320 for both cleaning and withdrawing medication.

Figure 15:
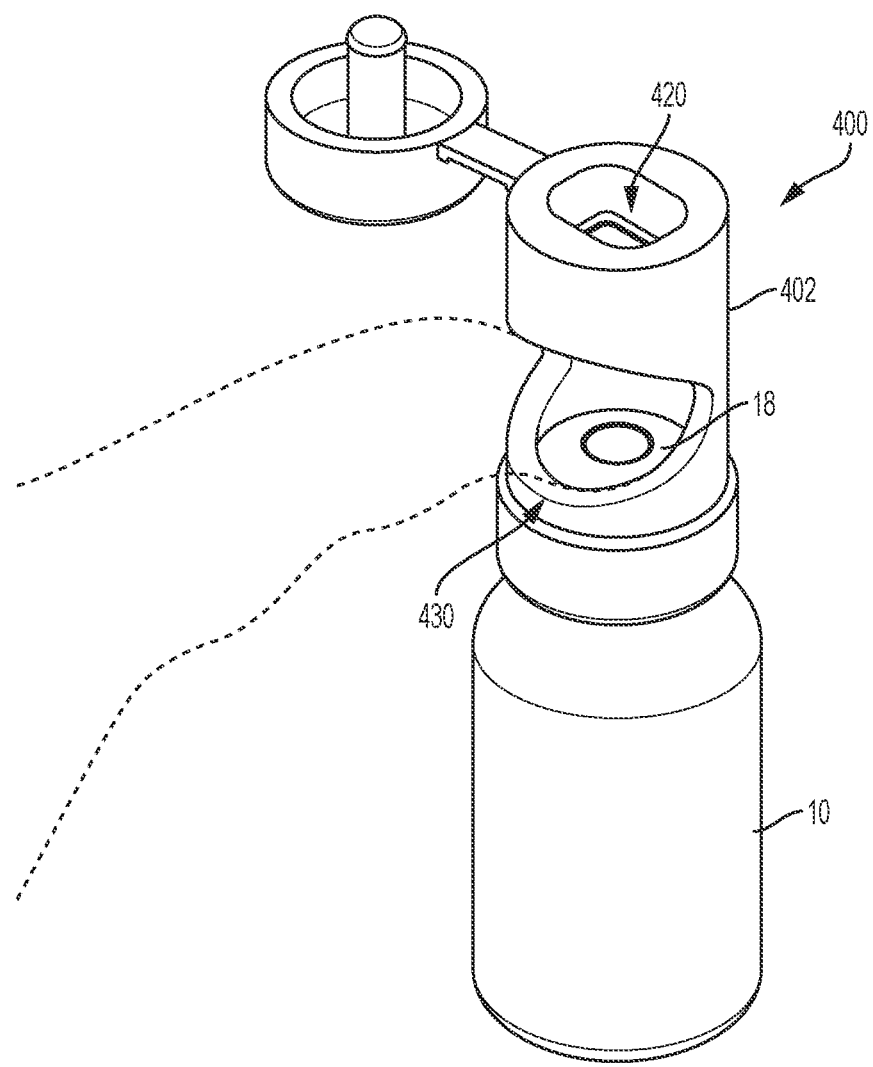
FIG. 15 is a perspective view of a fourth exemplary vial adaptor coupled to a vial.

Referring next to FIG. 15, a fourth exemplary vial adaptor 400 is shown for use with vial 10. Vial adaptor 400 is similar to the above-described vial adaptor 300, with like reference numerals identifying like elements, except as described below. The illustrative vial adaptor 400 includes a cleaning passageway 430 in side wall 402 that is distinct from needle opening 420. Cleaning passageway 430 is sized and shaped to allow a cleaning device (e.g., pad, wipe, swab) containing a disinfectant (e.g., alcohol), along with a user's finger (shown in broken lines), to access and clean stopper 18 of vial 10 before use.

Figure 16:
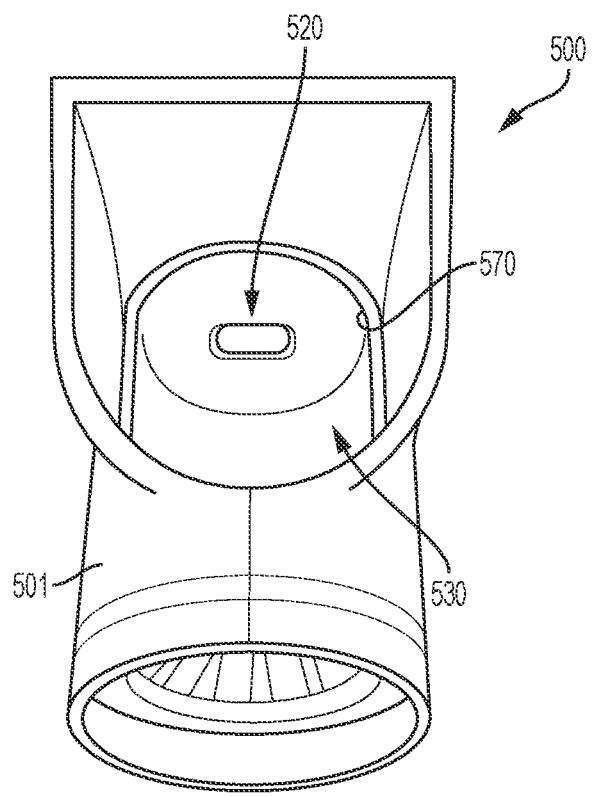
FIG. 16 is a perspective view of a fifth exemplary vial adaptor shown in a cleaning position.
Figure 17:
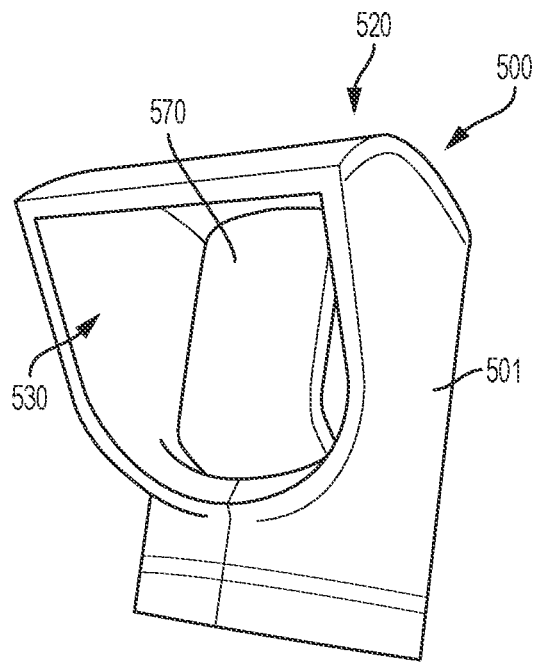
FIG. 17 is a perspective view of the vial adaptor of FIG. 16 shown in a withdrawing position.
Figure 18:
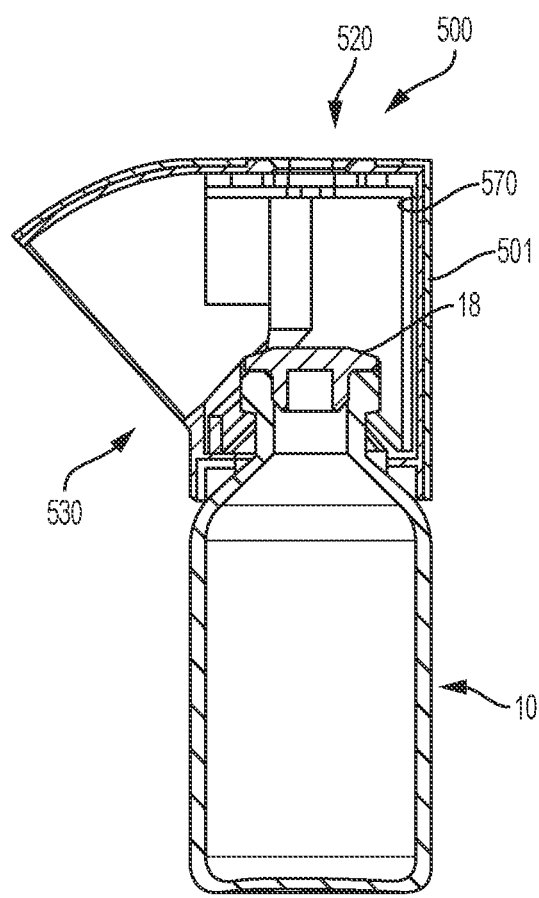
FIG. 18 is a cross-sectional view of another vial adaptor similar to the vial adaptor of FIG. 16 and shown in a cleaning position.
Figure 19:
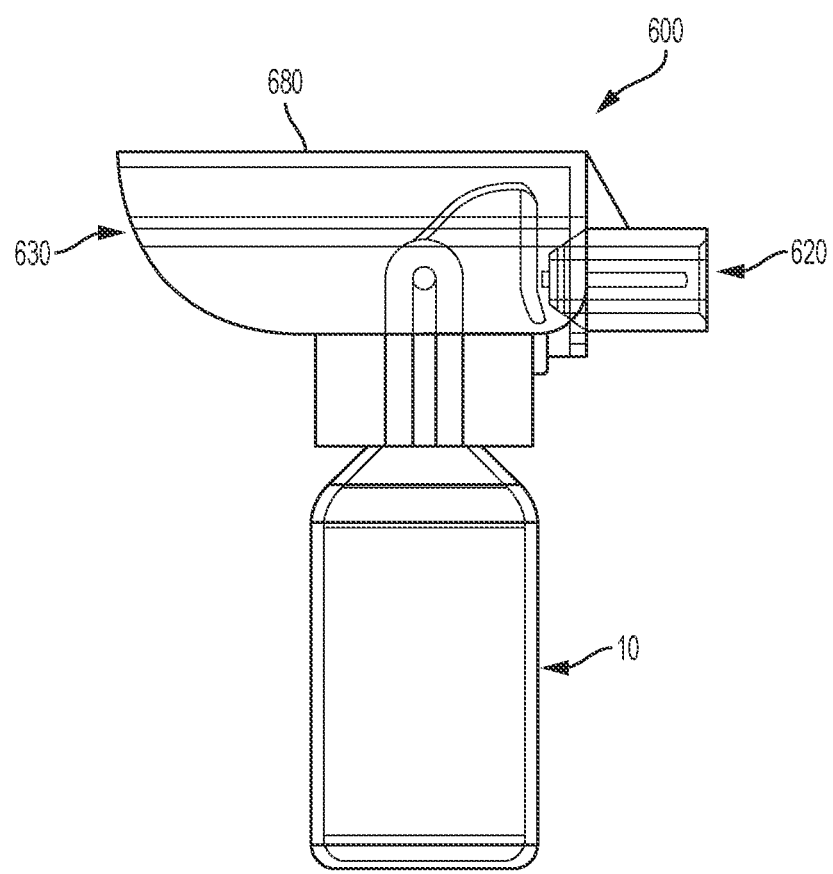
FIG. 19 is a front elevational view of a sixth exemplary vial adaptor coupled to a vial, the vial adaptor shown in a cleaning position.
Figure 20:
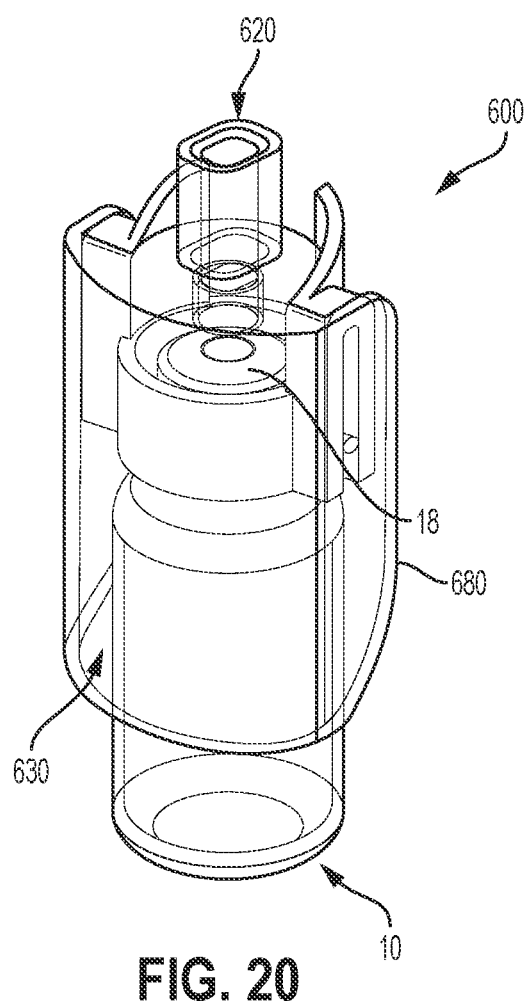
FIG. 20 is a perspective view of the vial adaptor of FIG. 19 shown in a withdrawing position.
Figure 21:
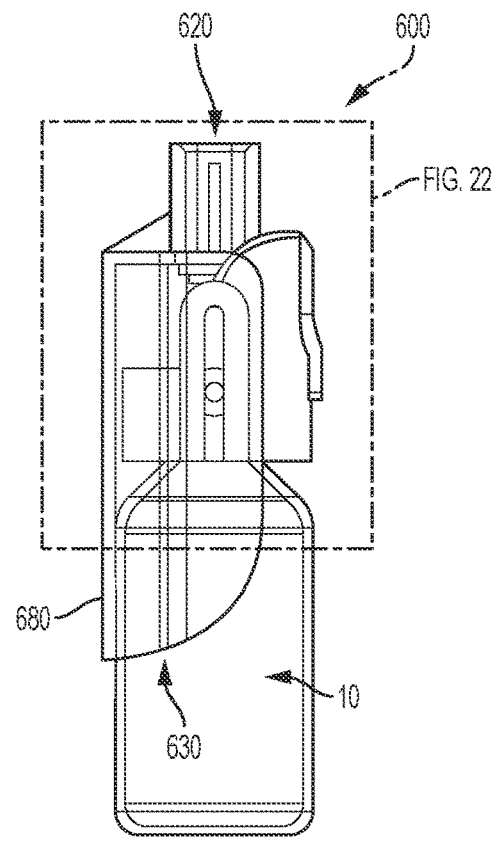
FIG. 21 is a front elevational view of the vial adaptor of FIG. 20.

Referring next to FIGS. 16-18, a fifth exemplary vial adaptor 500 is shown for use with vial 10. Vial adaptor 500 is similar to the above-described vial adaptors 100-400, with like reference numerals identifying like elements, except as described below. Vial adaptor 500 includes an outer body 501, a needle opening 520, and a distinct cleaning passageway 530. Additionally, vial adaptor 500 includes an inner body 570 rotatably disposed within outer body 501 between a cleaning position, as shown in FIGS. 16 and 18, and a withdrawal position, as shown in FIG. 17. In the cleaning position of FIG. 16, inner body 570 at least partially blocks access to needle opening 520 by narrowing and/or changing the shape of needle opening 520 while permitting access to cleaning passageway 530. In the cleaning position of FIG. 18, inner body 570 blocks needle opening 520 entirely while permitting access to cleaning passageway 530. In the withdrawal position of FIG. 17, inner body 570 rotates to expose needle opening 520 and block access to cleaning passageway 530. By distinguishing the cleaning process from the withdrawal process, vial adaptor 500 may reduce the risk of an unintentional needle stick injury to a user during the cleaning process.

Figure 22:
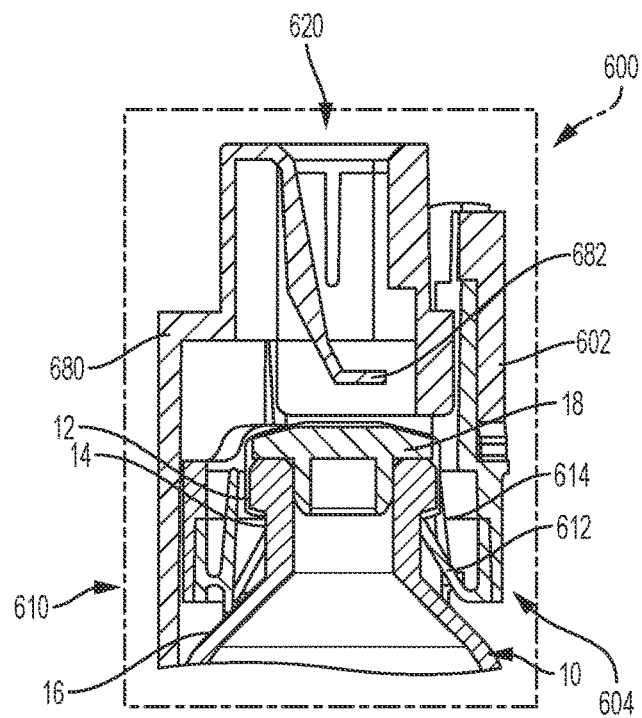
FIG. 22 is a detailed cross-sectional view of the vial adaptor of FIG. 21.

Referring next to FIGS. 19-22, a sixth exemplary vial adaptor 600 is shown for use with vial 10. Vial adaptor 600 is similar to the above-described vial adaptors 100-500, with like reference numerals identifying like elements, except as described below. Vial adaptor 600 includes a pivotable cover 680 that defines needle opening 620 on one end and cleaning passageway 630 on the other end. Cover 680 is rotatable between a cleaning position, shown in FIG. 19, and a withdrawal position, shown in FIGS. 20 and 21. In the cleaning position of FIG. 19, cover 680 rotates to a generally horizontal position. In this cleaning position, the user may be capable of accessing stopper 18 of vial 10 (FIG. 20) with a cleaning device through the generally horizontal cleaning passageway 630, but not with a needle through the generally horizontal needle opening 620. In the withdrawal position of FIGS. 20 and 21, cover 680 rotates to a generally vertical position. In this withdrawal position, the user may be capable of accessing stopper 18 of vial 10 with a needle through the generally vertical needle opening 620, but not with a cleaning device through the closed and generally vertical cleaning passageway 630. As shown in FIG. 22, one or more blocking members 682 may also be provided within cover 680 to further protect stopper 18 of vial 10 in the withdrawal position, until a geometrically corresponding needle assembly (not shown) enters needle opening 620, as discussed above, and moves (e.g., pivots) blocking member 682 out of the way. Again, by distinguishing the cleaning process from the withdrawal process, vial adaptor 600 may reduce the risk of an unintentional needle stick injury to a user during the cleaning process.

Vial adapter 600 is coupled to vial 10 using a coupling assembly 610 similar to the above-described coupling assembly 110 (FIG. 3). The illustrative coupling assembly 610 of FIG. 22 is positioned at or near lower end 604 of vial adapter 600 and includes a first set of relatively short and flexible fingers 612 and a second set of relatively long and flexible fingers 614, both of which extend radially inward from side wall 602 of vial adaptor 600 toward vial 10. As vial adaptor 600 is pressed downward onto vial 10, each finger 612 is designed to flex around flange 12 of vial 10 and then snap back or release toward neck 14, which locks vial adaptor 600 in place beneath flange 12 of vial 10. At the same time, each finger 614 is designed to flex over shoulder 16 while simultaneously abutting rim 12. Each flexed finger 614 may try to release by moving upward as far as possible along the narrowing, slanted shoulder 16 toward neck 14, which may apply a continuous upward force to vial adaptor 100 and maintain fingers 612 in contact with rim 12. The flexibility of fingers 612, 614, may allow coupling assembly 610 to accommodate vials 10 of different shapes and sizes.

Figure 23:
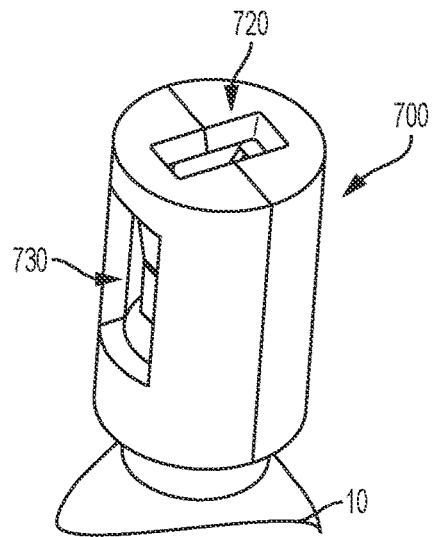
FIG. 23 is a perspective view of a seventh exemplary vial adaptor coupled to a vial.
Figure 24:
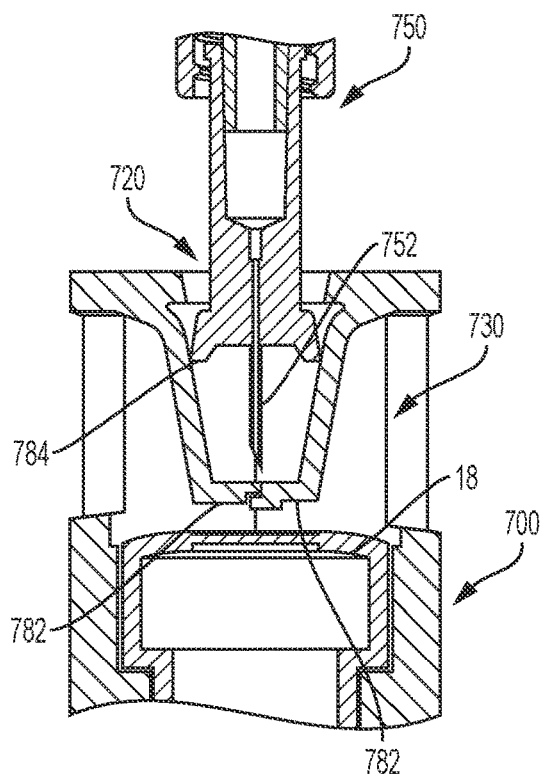
FIG. 24 is a cross-sectional view of the vial adaptor of FIG. 23 and a geometrically corresponding needle assembly, the vial adaptor shown in a non-use position.
Figure 25:
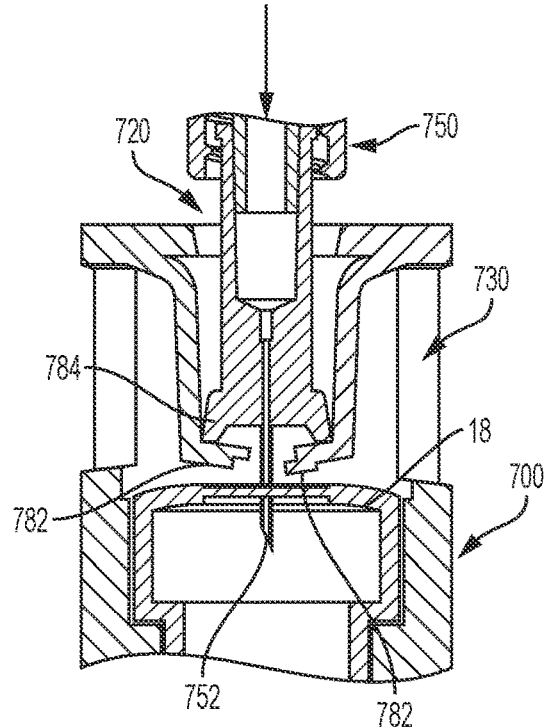
FIG. 25 is a cross-sectional view of the vial adaptor and the needle assembly of FIG. 24 shown in a use position.
Figure 26:
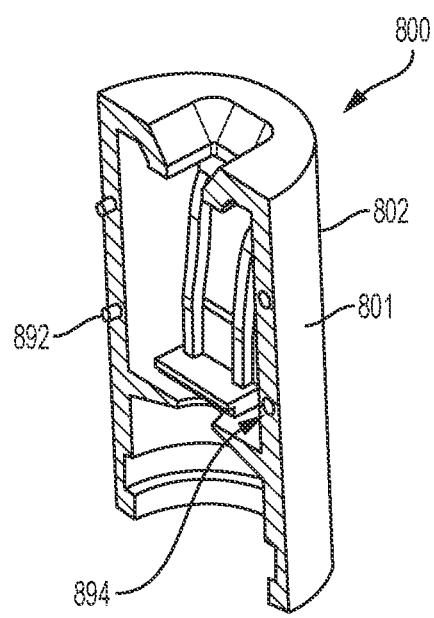
FIG. 26 is a perspective view of one half of an eighth exemplary vial adaptor.

Referring next to FIGS. 23-25, a seventh exemplary vial adaptor 700 and needle assembly 750 are shown for use with vial 10. Vial adaptor 700 and needle assembly 750 are similar to the above-described vial adaptors 100-600 and needle assembly 150-350, with like reference numerals identifying like elements, except as described below. The illustrative vial adaptor 700 includes one or more internal blocking members 782. The illustrative needle assembly 750 includes a needle 752 and one or more corresponding flanges 784. In a non-use position, as shown in FIG. 24, blocking members 782 are biased together to protect stopper 18 of vial 10. In a withdrawal position, as shown in FIG. 25, the geometrically corresponding needle assembly 750 enters needle opening 720, and flanges 784 move blocking members 782 apart to expose stopper 18 of vial 10 to needle 752. To clean vial 10, a disinfectant-containing cleaning device may be inserted through a distinct cleaning passageway 730 of vial adaptor 700, as discussed further above. Alternatively, a disinfectant-containing cleaning device that mimics the size and shape of needle assembly 750 may be provided for insertion between blocking members 782, such that the cleaning device would take the place of needle 752.

Figure 27:
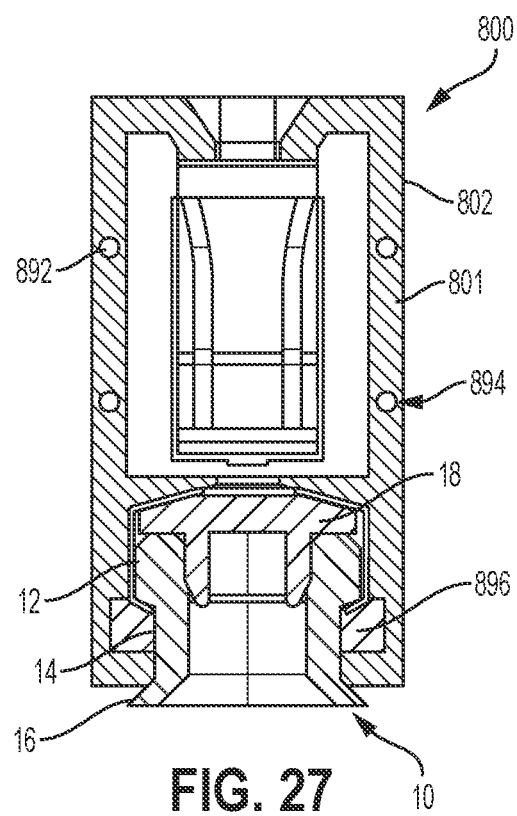
FIG. 27 is an elevational view of the vial adaptor of FIG. 26.
Figure 28:
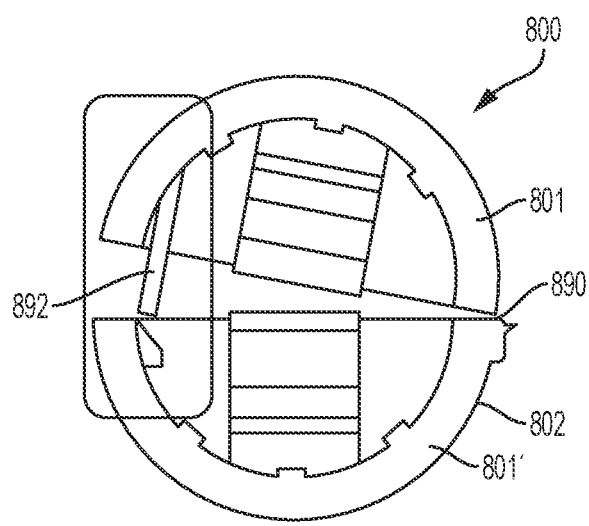
FIG. 28 is a plan view of two halves of the vial adaptor of FIG. 26 coupled together with a hinge.
Figure 29:
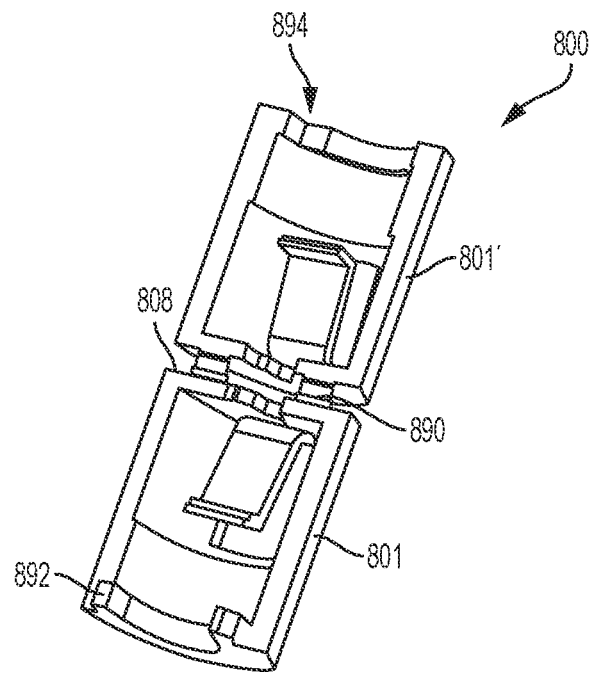
FIG. 29 is a perspective view of two halves of the vial adaptor of FIG. 26 coupled together with a hinge.

Referring next to FIGS. 26-29, an eighth exemplary vial adaptor 800 is shown for use with vial 10. Vial adaptor 800 is similar to the above-described vial adaptors 100-700, with like reference numerals identifying like elements, except as described below. The illustrative vial adaptor 800 includes a two-piece body made from body pieces 801, 801'. On one side, body pieces 801, 801' may be coupled together using a flexible hinge 890. In the illustrated embodiment of FIG. 28, the hinge 890 is located along side wall 802 of vial adaptor 800. In the illustrated embodiment of FIG. 29, the hinge 890 is located along upper wall 808 of vial adaptor 800. On the other side, body pieces 801, 801' may be coupled together using one or more fasteners, such as pegs 892 on body piece 801 that are received within recesses 894 in the other body piece 801'. It is also within the scope of the present disclosure for the body pieces 801, 801' to be welded, adhered, or otherwise coupled together around vial 10. A gasket 896 may be provided that fits into neck 14 of vial 10 between flange 12 and shoulder 16, as shown in FIG. 27, to seal vial adaptor 800 onto vial 10.

Various features of the above-described vial adaptors 100-800 may be mixed and matched. For example, vial adaptor 100 of FIGS. 2-9 may include a partial-length side wall similar to side wall 202 of FIGS. 11 and 12, a cap similar to cap 360 of FIGS. 13 and 14, a coupling assembly similar to coupling assembly 610 of FIG. 22, one or more blocking members similar to blocking members 782 of FIGS. 24-25, and/or a gasket similar to gasket 896 of FIG. 27.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of using a vial adaptor coupled to a vial, the method comprising:
providing a vial adaptor configured for use with a vial containing a medication and a needle assembly having a needle, the vial adaptor having a substantially hollow body configured to couple to the vial, a cleaning passageway in the body, and a shroud extending outwardly from the body to block needle insertion into the vial through the cleaning passageway, the body including a side wall and an upper wall, the cleaning passageway having an inlet in the side wall, the side wall deviating radially outwardly to follow the path of the shroud wherein the inlet deviates radially outwardly from a lower end of the inlet to an upper end of the inlet, the side wall including a rounded portion, a first flat portion, and a second flat portion positioned opposite the first flat portion, the first and second flat portions extending radially outwardly from the rounded portion;
cleaning a stopper of the vial by inserting a disinfectant-containing cleaning device through the cleaning passageway of the vial adaptor; and
withdrawing a medication from the vial by inserting a needle through a needle opening of the vial adaptor and into the stopper of the vial.

2. The method of claim 1, further comprising, prior to the cleaning, removing a cap from the vial through the cleaning passageway.

3. The method of claim 1, further comprising blocking needle insertion into the stopper of the vial through the cleaning passageway with the shroud around the cleaning passageway.

4. The method of claim 1, wherein the needle opening is arranged along an axis and is sized and shaped to receive the needle along the axis to withdraw the medication from the vial, and the shroud extends radially outward from the axis.

5. The method of claim 4, wherein access to the stopper of the vial through the cleaning passageway is offset from the axis of the needle opening between a first angle measured through the upper end of the inlet and a second angle measured through the lower end of the inlet.

6. The method of claim 5, wherein the first angle is about 60 degrees to about 70 degrees and the second angle is about 110 degrees to about 120 degrees.

7. The method of claim 1, wherein the needle opening follows a linear pathway to the stopper and the cleaning passageway follows a non-linear pathway to the stopper.

8. The method of claim 1, further comprising providing a needle assembly including a hub and the needle coupled to the hub, wherein the hub has a keyed outer profile that matches the shape of the needle opening, and wherein the withdrawing further includes inserting the hub into the needle opening.

9. The method of claim 1, wherein the height between the stopper and a top of the needle opening is between about 15 mm and about 25 mm.

10. The method of claim 1, wherein the needle opening is arranged along an axis, and the first and second flat portions and the rounded portion of the side wall are positioned in a plane perpendicular to the axis between the lower end of the inlet and the upper end of the inlet.

11. The method of claim 1, wherein the shroud is positioned between the first and second flat portions and cooperates with the first and second flat portions to define the inlet of the cleaning passageway.

12. The method of claim 1, wherein the medication is an insulin.

13. The method of claim 1, wherein the vial includes a flange, a neck beneath the flange, and a shoulder beneath the neck, the method further comprising coupling the body to the vial by:
flexing a plurality of first fingers of a coupling assembly of the vial adaptor over the flange of the vial to release the plurality of first fingers beneath the flange; and
contacting the shoulder of the vial with a plurality of second fingers of the coupling assembly to bias the plurality of first fingers toward the flange of the vial.

14. A vial adaptor configured for use with a vial containing a medication and a needle assembly having a needle, the vial adaptor comprising:
a substantially hollow body configured to couple to the vial, the body including a needle opening arranged along an axis and a cleaning passageway, the needle opening being sized to receive the needle along the axis to withdraw the medication from the vial; and
a shroud extending outwardly from the body to block needle insertion into the vial through the cleaning passageway,
wherein the body includes a side wall and an upper wall and the cleaning passageway has an inlet in the side wall, the side wall deviating radially outwardly to follow the path of the shroud wherein the inlet deviates radially outwardly from a lower end of the inlet to an upper end of the inlet, the side wall including a rounded portion, a first flat portion, and a second flat portion positioned opposite the first flat portion, the first and second flat portions extending radially outwardly from the rounded portion.

15. The vial adaptor of claim 14, wherein access to a stopper of the vial through the cleaning passageway is offset from the axis of the needle opening between a first angle measured through the upper end of the inlet and a second angle measured through the lower end of the inlet.

16. The vial adaptor of claim 15, wherein the needle opening follows a linear pathway to the stopper and the cleaning passageway follows a non-linear pathway to the stopper.

17. The vial adaptor of claim 14, wherein the first and second flat portions and the rounded portion of the side wall are positioned in a plane perpendicular to the axis between the lower end of the inlet and the upper end of the inlet.

18. The vial adaptor of claim 14, wherein the shroud is positioned between the first and second flat portions and cooperates with the first and second flat portions to define the inlet of the cleaning passageway.

* * * * *